(12) United States Patent
Wu et al.

(10) Patent No.: US 10,416,091 B2
(45) Date of Patent: Sep. 17, 2019

(54) DEFECT INSPECTION METHOD AND APPARATUS USING MICRO LENS MATRIX

(71) Applicants: SEMICONDUCTOR MANUFACTURING INTERNATIONAL (SHANGHAI) CORPORATION, Shanghai (CN); SEMICONDUCTOR MANUFACTURING INTERNATIONAL (BEIJING) CORPORATION, Beijing (CN)

(72) Inventors: Qiang Wu, Shanghai (CN); Wei Xiong, Shanghai (CN); Xuan Li, Shanghai (CN)

(73) Assignees: SEMICONDUCTOR MANUFACTURING INTERNATIONAL (SHANGHAI) CORPORATION, Shanghai (CN); SEMICONDUCTOR MANUFACTURING INTERNATIONAL (BEIJING) CORPORATION, Beijing (CN)

( * ) Notice: Subject to any disclaimer, the term of this patent is extended or adjusted under 35 U.S.C. 154(b) by 12 days.

(21) Appl. No.: 15/706,409

(22) Filed: Sep. 15, 2017

(65) Prior Publication Data

US 2018/0080883 A1 Mar. 22, 2018

(30) Foreign Application Priority Data

Sep. 18, 2016 (CN) .......................... 2016 1 0826112

(51) Int. Cl.
*G01N 21/956* (2006.01)
*G01N 21/95* (2006.01)
(Continued)

(52) U.S. Cl.
CPC ...... *G01N 21/9501* (2013.01); *G01N 21/8806* (2013.01); *G01N 21/956* (2013.01);
(Continued)

(58) Field of Classification Search
CPC .......... G01N 2035/00326; G01N 2035/00495; G01N 21/6428; G01N 35/00;
(Continued)

(56) References Cited

U.S. PATENT DOCUMENTS 6,011,860 A 1/2000 Fujieda et al.
6,192,168 B1 2/2001 Feldstein et al.
(Continued)

FOREIGN PATENT DOCUMENTS

CN 101960293 A 1/2011
CN 102256100 A 11/2011
(Continued)

OTHER PUBLICATIONS

European Patent Application No. 17191253.8, Partial European Search Report dated Mar. 16, 2018, 14 pages.
(Continued)

*Primary Examiner* — Michael P Stafira
(74) *Attorney, Agent, or Firm* — Kilpatrick Townsend & Stockton LLP

(57) ABSTRACT

A substrate surface defect detection device includes an optical waveguide for receiving first light and directing the received first light to a surface of a to be tested substrate, the optical waveguide having a first surface facing toward the substrate and a second surface facing away from the substrate, a microlens array disposed on the second surface of the optical waveguide, the microlens array including a plurality of microlenses arranged in an array for receiving second light from the surface of the to be tested substrate and converging the received second light to converged light, and
(Continued)

an imaging component for receiving the converged light from the at least one microlens array for optical imaging. The substrate surface defect detection device requires significantly less time than conventional substrate surface defect detection devices.

25 Claims, 10 Drawing Sheets

(51) Int. Cl.
| | |
|---|---|
| *G01N 21/88* | (2006.01) |
| *G06T 7/00* | (2017.01) |
| *G02B 3/00* | (2006.01) |
| *G06T 5/00* | (2006.01) |
| *H01L 21/66* | (2006.01) |

(52) U.S. Cl.
CPC ............ *G02B 3/0037* (2013.01); *G06T 5/006* (2013.01); *G06T 7/0002* (2013.01); *G06T 7/0004* (2013.01); *G06T 7/0008* (2013.01); G01N 2201/0638 (2013.01); G06T 2207/10052 (2013.01); G06T 2207/30121 (2013.01); G06T 2207/30148 (2013.01); H01L 22/12 (2013.01)

(58) Field of Classification Search
CPC ........... G01N 35/0092; G01N 2201/12; G01N 2015/1006; G01N 21/25; G01N 21/648; G01N 35/1065; G01N 15/1475; G01N 2021/6439; G01N 2021/6463; G01N 2035/00138; G01N 2035/00356; G01N 2035/00366; G01N 2035/00425; G01N 2035/0449; G01N 2035/0486; G01N 2035/0491; G01N 2201/024; G01N 2201/04; G01N 2201/08; G01N 33/54366; G01N 35/00029; G01N 35/00069; G01N 35/026; G01N 35/04; G01N 35/10; G01N 35/1011; G01N 35/1072; G01N 2015/0073; G01N 2015/008; G01N 2015/1486; G01N 2021/6419; G01N 2021/6421; G01N 2035/00148; G01N 2035/0237; G01N 2035/00306; G01N 2035/00435; G01N 2035/00633; G01N 2035/0474; G01N 2035/0493; G01N 2035/0494; G01N 21/27; G01N 21/6408; G01N 33/5005; G01N 33/54306; G01N 33/54313; G01N 33/56983; G01N 33/62; G01N 33/6827; G01N 33/80; G01N 33/92; G01N 35/00623; G01N 35/00871; G01N 35/1009; G01N 21/6454; G01N 2201/0696; G01N 2201/0638; G01N 33/54373; G01N 2035/00277; G01N 2035/00811; G01N 2035/0094; G01N 2035/103; G01N 21/6452; G01N 21/7703; G01N 2201/06113; G01N 35/00732; G01N 2021/513; G01N 2021/6417; G01N 2021/6441; G01N 2021/6478; G01N 2021/6482; G01N 2030/8827; G01N 2035/1048; G01N 21/0303; G01N 21/07; G01N 21/51; G01N 21/64; G01N 21/76; G01N 21/7743; G01N 21/8806; G01N 21/9501; G01N 21/956; G01N 2201/0446; G01N 2201/062; G01N 2333/43578; G01N 30/02; G01N 30/88; G01N 33/48; G01N 33/50; G01N 33/5436; G01N 33/54386; G01N 33/544; G01N 33/559; G01N 33/566; G01N 33/86; G01N 35/02
See application file for complete search history.

(56) References Cited

U.S. PATENT DOCUMENTS

| | | |
|---|---|---|
| 6,618,494 B1 | 9/2003 | Nonay et al. |
| 8,221,700 B2* | 7/2012 | Steinmiller ....... B01L 3/502707 |
| | | 422/503 |
| 2007/0029277 A1* | 2/2007 | Jacobowitz ...... B29D 11/00365 |
| | | 216/24 |
| 2011/0168918 A1 | 7/2011 | Wimberger-Friedl et al. |
| 2015/0010265 A1* | 1/2015 | Popovich ............ G02F 1/13342 |
| | | 385/10 |

FOREIGN PATENT DOCUMENTS

| | | |
|---|---|---|
| WO | 9929117 | 6/1999 |
| WO | 0044181 | 7/2000 |
| WO | 2009107041 | 9/2009 |

OTHER PUBLICATIONS

European Patent Application No. 17191253.8, Extended European Search Report dated May 15, 2018, 15 pages.
Chinese Patent Application No. 201610826112.1, First Office Action dated Jun. 25, 2019, 26 pages (English translation included).

* cited by examiner

DEFECT INSPECTION METHOD AND APPARATUS USING MICRO LENS MATRIX

CROSS-REFERENCES TO RELATED APPLICATIONS

The present application claims priority to Chinese patent application No. 201610826112.1, filed on Sep. 18, 2016, the content of which is incorporated herein by reference in its entirety.

FIELD OF THE INVENTION

The present disclosure relates to semiconductor technology. More particularly, embodiments of the present disclosure relate to a substrate surface defect detection apparatus and method, an image distortion correction method and apparatus, and a system including a substrate surface defect detection apparatus and an image distortion correction apparatus.

BACKGROUND OF THE INVENTION

FIG. 1A is a perspective view of a conventional substrate surface defect detection system 102. FIG. 1B is a plan view of a substrate 101 shown in FIG. 1A. As known in the art, the surface defects of a substrate 101 need to be detected using a sophisticated and complex optical system 102. FIG. 1B schematically shows the exposure area of substrate 101 and the effective field of view of substrate surface defect detection system 102. The effective field of view of substrate surface defect detection system 102 is typically about 30 μm×30 μm. If system 102 is used to detect surface defects of substrate 101 having a typical exposure area of 26 mm×33 mm, about one million operations must be performed to complete the surface defects detection (e.g., each shot only takes a field of view picture). If the time required to take a picture plus the time required to move the detection system between the different shots takes 0.5 second, it will take 50 million seconds, i.e., about 139 hours to take pictures of the entire exposure area. It can be seen that the efficiency of current substrate surface defect detection systems and methods is low.

BRIEF SUMMARY OF THE INVENTION

In accordance with the present disclosure, a novel substrate surface defect detection apparatus is provided that can significantly improve the detection speed of substrate surface defects.

Embodiments of the present disclosure also provide an image distortion correction method and apparatus that are capable of correcting distortion of an image output from a substrate surface defect detection apparatus.

Embodiments of the present disclosure also provide substrate surface defect detection and image correction system.

Embodiments of the present disclosure also provide an apparatus and method for efficiently detecting substrate surface defects that can reduce the cost of defect detection.

In accordance to the present disclosure, a substrate surface defect detection device may include an optical waveguide for receiving first light and directing the received first light to a surface of a to be tested substrate, the optical waveguide having a first surface facing toward the substrate and a second surface facing away from the substrate; at least one microlens array disposed on the second surface of the optical waveguide, the at least one microlens array comprising a plurality of microlenses arranged in an array for receiving second light from the surface of the to be tested substrate and converging the received second light to converged light; and an imaging component for receiving the converged light from the at least one microlens array for imaging.

In one embodiment, the imaging component includes a plurality of imaging units, each of the imaging units comprising a plurality of pixels, each of the imaging units being associated with one of the microlenses to receive a portion of the converged light.

In one embodiment, the at least one microlens array includes a first microlens array and a second microlens array stacked over each other. Each of the first and second microlens arrays has a plurality of microlenses, each of the microlenses of the first microlens array has an optical axis aligned to an optical axis of one corresponding microlens of the second microlens array.

In one embodiment, the substrate surface defect detection device may further include a plurality of light confinement members disposed between a corresponding imaging unit and a corresponding microlens and configured to enable light from the corresponding microlens to reflect a specific field of view to pass therethrough and into the corresponding imaging unit.

In one embodiment, the light confinement members each comprise a light blocking plate. In one embodiment, the light confinement members each include a cylindrical optical member having a light receiving surface and a light exit surface.

In one embodiment, the at least one microlens array further comprises a support member disposed at an edge of the microlenses. In one embodiment, the at least one microlens array includes a first microlens array and a second microlens array stacked over each other, and the support member of the first microlens array and the support member of the second microlens array are aligned with each other.

In one embodiment, the support member is formed of a same material as a material of the microlenses and includes a barrier layer on a lower surface for blocking light from entering the support member. In one embodiment, the barrier layer includes a metal plating layer.

In one embodiment, the support member is formed of a same material as a material of the microlenses, and a surface portion of the optical waveguide below the support member includes a barrier layer for blocking light from entering the support member.

In one embodiment, each of the microlenses includes a plano-convex lens. The coordinates of a point on an aspheric surface of the plano-convex lens in a z-direction parallel to an optical axis has a second order function term and a fourth order function term of a distance from a corresponding plane projection point perpendicular to the optical axis.

In one embodiment, the aspheric surface of the plano-convex lens is calculated by the following expression:

$$Z = \frac{\frac{1}{R}r^2}{1+\sqrt{1-(1+K)\frac{r^2}{R^2}}} + \alpha_1 r^2 + \alpha_2 r^4$$

where r is a distance from a point of the aspheric surface perpendicular to the optical axis, Z is the coordinate of the point on the aspheric surface of the lens in the Z-direction, R is the radius of curvature from the optical axis to the lens surface, K is a conic constant, α1 is an aspheric surface coefficient of the second order function term, and α2 is an aspheric surface coefficient of the fourth order function term.

In one embodiment, the optical waveguide includes a first incident surface and a second incident surface disposed on opposite sides of the optical waveguide; the first light includes third light and fourth light, the third light entering the optical waveguide from the first incident surface and the fourth light entering the optical waveguide from the second incident surface.

In one embodiment, the first incident surface and the second incident surface are inclined with respect to the first surface of the optical waveguide.

In one embodiment, the substrate surface defect detection device may further include a laser light source for generating a laser beam; a semitransparent mirror disposed at an angle relative to an optical axis of the laser beam for splitting the laser beam into first partial light and second partial light; and a first light generating member for generating a first beam and including a first beam expander for expanding the first partial light in a first dimension to generate a first laser beam, a first lens for converging the first laser beam in a second dimension different from the first dimension to generate a converged first laser beam, and a first mirror for reflecting the converged first laser beam as the third light entering the optical waveguide from the first incident surface.

In one embodiment, the substrate surface defect detection device may further include a second mirror for reflecting the second partial light, and a second light generating member for generating a second beam that includes a second beam expander for expanding the second partial light in the first dimension to generate a second laser beam, a second lens for converging the second laser beam in the second dimension to generate a converged second laser beam, and a third mirror for reflecting the converged second laser beam as the fourth light entering the optical waveguide from the second incident surface.

In one embodiment, the third light and the fourth light have a same light intensity.

In one embodiment, the substrate surface defect detection device may further include a spacer disposed on a side of the at least one microlens array and configured to block ambient light from entering the microlenses.

In one embodiment, a sum of a thickness of the optical waveguide, a thickness of the at least one microlens array, and an air gap between the optical waveguide and the at least one microlens array is less than or equal to 20 μm.

In one embodiment, an air gap between the surface of the to be tested substrate and the light receiving surface of the cylindrical optical member is less than or equal to 20 μm.

In one embodiment, each of the microlenses has a diameter in a range between 5 μm and 20 μm.

In one embodiment, the optical waveguide includes a plurality of scattering elements configured to scatter light transmitted by the optical waveguide onto the surface of the to be tested substrate.

In one embodiment, the at least one microlens array further includes a plurality of support members disposed at an edge of the microlenses and configured to support corresponding microlenses disposed thereon. Each of the plurality of scattering elements is disposed at a location of a corresponding one of the plurality of support members.

In one embodiment, the substrate is one of a semiconductor wafer, a semiconductor substrate, and a display panel. In one embodiment, the optical waveguide, the at least one microlens array, and the imaging component are configured such that a spot from light of a desired imaging portion of the surface of the to be tested substrate incident on an imaging plane of the imaging component through the optical waveguide and the at least one microlens array is smaller than a size of an Airy disk.

Embodiments of the present disclosure also provide a method for correcting image distortion. The image distortion correcting method may include obtaining a first light intensity of each pixel in an image comprising a plurality of pixels, the plurality of pixels including a center pixel at the center or in a vicinity of the center of the image and a first pixel different from the center pixel, calculating a first distance between the first pixel and the center pixel, calculating a second distance between a second pixel and the center pixel, the second pixel comprising at least a portion of pixels adjacent to the first pixels, and correcting a light intensity of the first pixel based on the first light intensity of the first pixel, the first distance, the second distance, and the first light intensity of the second pixel.

In one embodiment, the first pixel has coordinates (i, j), the center pixel has coordinates (0, 0), and the light intensity of the first pixel is corrected according to the following expression:

$$\overline{P_{(i,j)}} = C_1 P_{(i,j)} + C_2 P_{(i-1,j-1)} + C_3 P_{(i-1,j)} + C_4 P_{(i,j-1)}$$

where i, j are non-zero integers, C1, C2, C3, C4 are the correction coefficients and C1+C2+C3+C4=1, is the light intensity of the first pixel (i, j), and is the corrected light intensity of the pixel (i, j), and a pixel (i−1, j−1), a pixel (i−1, j), and a pixel (i, j−1) are pixels that are closer to the center pixel (0, 0) than the first pixel (i, j).

In one embodiment, the first pixel has coordinates (i, j), the center pixel has coordinates (0, 0), and the light intensity of the first pixel is corrected according to the following expression:

$$\overline{P_{(i,j)}} = C_1 P_{(i,j)} + C_2 P_{(i-1,j-1)} + C_3 P_{(i-1,j)} + C_4 P_{(i,j-1)}$$

where i, j are non-zero integers, C1, C2, C3, C4 are the correction coefficients and C1+C2+C3+C4=1, is the light intensity of the first pixel (i, j), and is the corrected light intensity of the pixel (i, j), and a pixel (i+1, j+1), a pixel (i+1, j), and a pixel (i, j+1) are pixels that are father away from the center pixel (0, 0) than the first pixel (i, j).

Embodiments of the present disclosure further provide an apparatus for correcting image distortion. The apparatus may includes an obtaining unit configured to obtain a first light intensity of each pixel in an image comprising a plurality of pixels, the plurality of pixels including a center pixel at the center or in a vicinity of the center of the image and a first pixel different from the center pixel, a first calculation unit configured to calculate a first distance between the first pixel and the center pixel, a second calculation unit configured to calculate a second distance between a second pixel and the center pixel, the second pixel comprising at least a portion of pixels adjacent to the first pixels, and a correction unit configured to correct a light intensity of the first pixel based on the first light intensity of the first pixel, the first distance, the second distance, and the first light intensity of the second pixel.

Embodiments of the present disclosure may also provide an apparatus that includes both the substrate surface defect detection device and the image distortion correcting device described above.

The following description, together with the accompanying drawings, will provide a better understanding of the nature and advantages of the claimed disclosure.

BRIEF DESCRIPTION OF THE DRAWINGS

The accompanying drawings, which are included to provide a further understanding of the invention and are incorporated in and constitute a part of this application, illustrate certain embodiments of the invention. In the drawings.

DETAILED DESCRIPTION OF THE INVENTION

Figure 1A:
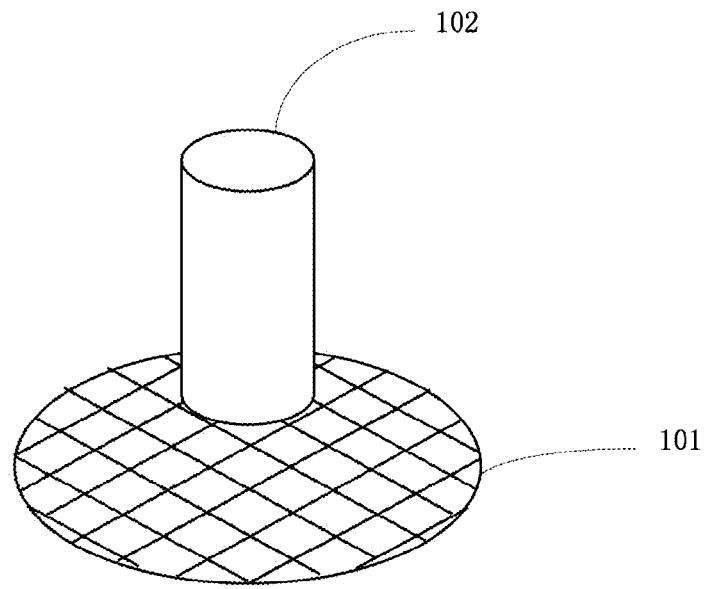
FIG. 1A is a perspective view of an optical system for substrate surface defects detection according to the prior art.
Figure 1B:
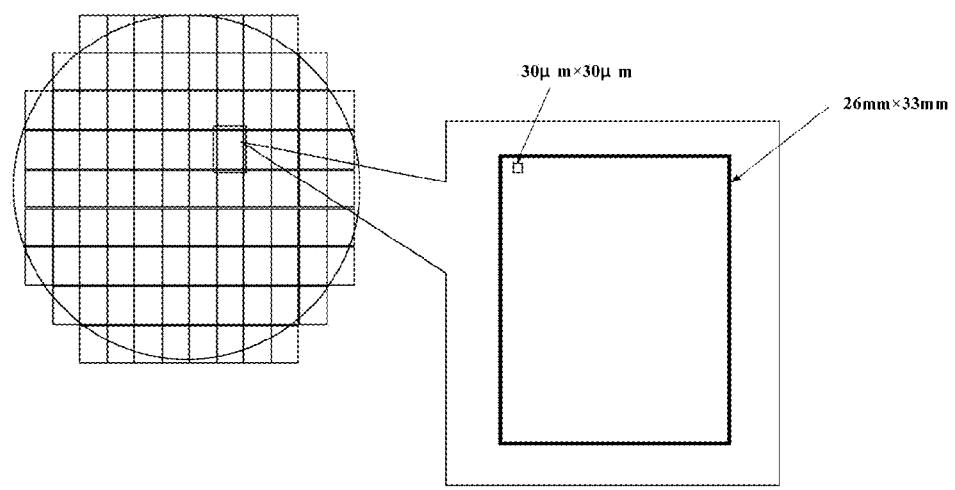
FIG. 1B is a plan view illustrating a substrate and the field of view of the optical system shown in FIG. 1A.

In the following description, numerous specific details are provided for a thorough understanding of the present invention. However, it should be appreciated by those of skill in the art that the present invention may be realized without one or more of these details. In other examples, features and techniques known in the art will not be described for purposes of brevity.

It should be understood that the drawings are not drawn to scale, and similar reference numbers are used for representing similar elements. Embodiments of the invention are described herein with reference to cross-section illustrations that are schematic illustrations of idealized embodiments (and intermediate structures) of the invention. The thickness of layers and regions in the drawings may be exaggerated relative to each other for clarity. Additionally, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

It will be understood that, when an element or layer is referred to as "on," "disposed on," "adjacent to," "connected to," or "coupled to" another element or layer, it can be disposed directly on the other element or layer, adjacent to, connected or coupled to the other element or layer, or intervening elements or layers may also be present. In contrast, when an element is referred to as being "directly on," directly disposed on," "directly connected to," or "directly coupled to" another element or layer, there are no intervening elements or layers present between them. It will be understood that, although the terms "first," "second," "third," etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present disclosure.

Relative terms such as "under," "below," "underneath," "over," "on," "above," "bottom," and "top" are used herein to described a relationship of one element, layer or region to another element, layer or region as illustrated in the figures. It will be understood that these terms are intended to encompass different orientations of the structure in addition to the orientation depicted in the figures. For example, if the device shown in the figures is flipped, the description of an element being "below" or "underneath" another element would then be oriented as "above" the other element. Therefore, the term "below," "under," or "underneath" can encompass both orientations of the device. Because devices or components of embodiments of the present disclosure can be positioned in a number of different orientations (e.g., rotated 90 degrees or at other orientations), the relative terms should be interpreted accordingly.

The terms "a", "an" and "the" may include singular and plural references. It will be further understood that the terms "comprising", "including", having" and variants thereof, when used in this specification, specify the presence of stated features, steps, operations, elements, and/or components, but do not preclude the presence or addition of one or more other features, steps, operations, elements, components, and/or groups thereof. Furthermore, as used herein, the words "and/or" may refer to and encompass any possible combinations of one or more of the associated listed items.

The use of the terms first, second, etc. do not denote any order, but rather the terms first, second, etc. are used to distinguish one element from another. Furthermore, the use of the terms a, an, etc. does not denote a limitation of quantity, but rather denote the presence of at least one of the referenced items.

The term "vertical" as used in this application is defined as a plane perpendicular to the conventional plane or surface of a wafer or substrate, regardless of the orientation of the wafer or substrate. The term "horizontal" refers to a direction perpendicular to the vertical as defined above.

It should be noted that similar parts are given reference numerals and symbols as similar as possible throughout the drawings. Once a part has been defined and described, it will not be described again in subsequent drawings.

In the present disclosure, a substrate may include one or more wafers selected from a group consisting of a semiconductor wafer, a semiconductor substrate, and a display panel.

The present disclosure will be described by way of illustrating embodiments with reference to the accompanying drawings.

Figure 2A:
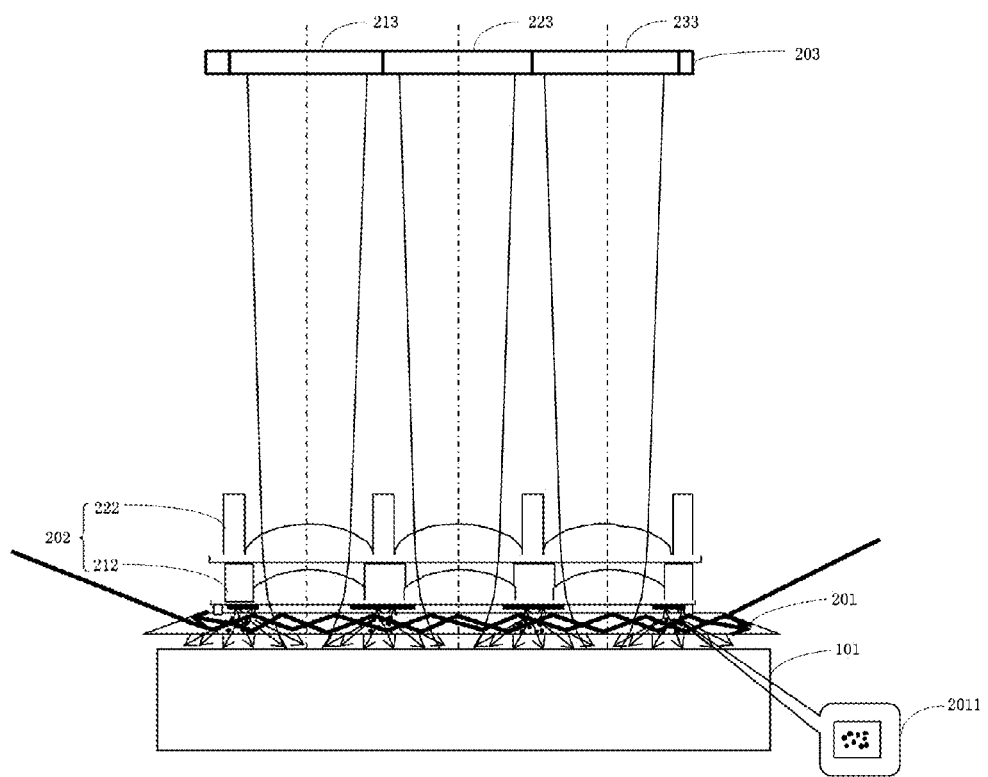
FIG. 2A is a schematic cross-sectional view of a substrate surface defect detection apparatus according to an embodiment of the present disclosure.

FIG. 2A is a schematic cross-sectional view of a substrate surface defect detection device according to an embodiment of the present disclosure. As shown in FIG. 2A, the substrate surface defect detection device may include an optical waveguide 201, at least one microlens array 202, and an imaging component 203. The substrate surface defect detection device will be described in detail below.

Optical waveguide 201 is configured to receive light and direct light to the surface of a to be tested substrate 101. Optical waveguide 201 has a first surface adjacent to (facing toward) substrate 101 and a second surface opposite the first surface (i.e., facing away from the substrate). Microlens array 202 is arranged on the side of optical waveguide 201 opposite substrate 101, i.e., microlens 202 is disposed on the side where the second surface of optical waveguide 201 is located. Imaging component 203 is configured to receive light from the microlens array for imaging.

In one embodiment, optical waveguide 201 may include a plurality of scattering elements 2011 configured to scatter the light transmitted in optical waveguide 201 onto the surface of the to be tested substrate 101. The scattering elements 2011 may be obtained by ion bombardment of optical waveguide 201, or by laser focusing to local portions of optical waveguide 201 in such a manner that the local portions of optical waveguide 201 are melted.

In one embodiment, microlens array 202 may be glued together with optical waveguide 201. The at least one microlens array 202 may include a first microlens array 212 and a second microlens array 222 stacked on top of each other, as shown in FIG. 2A. In one embodiment, the at least one microlens array 202 may be configured such that the optical axis of the microlenses in one microlens array is aligned with the optical axis of the corresponding microlenses in another microlens array (as indicated by the dotted lines shown in FIG. 2A). Each microlens array includes a plurality of microlenses arranged in an array for receiving and converging light from the surface of the to be tested substrate passing through optical waveguide 201. In one embodiment, the diameter of a microlens may be in the range between 5 µm and 20 µm, e.g., 10 µm.

It is to be understood that microlens array 202 may include multiple microlens arrays, such as a third microlens array (not shown) disposed on second microlens array 222, and adjacent microlens arrays may be glued together. In one embodiment, the microlens array may also include a support member (e.g., a cylindrical member) disposed at the peripheral edge of the microlens that can be used to support a microlens adjacent thereto. In one embodiment, the support member (shown as a protrusion having a rectangular shape in FIG. 2A) of first microlens array 212 and the support member of second microlens array 222 are aligned with each other, as shown in FIG. 2A. In the case where optical waveguide 201 includes a plurality of scattering elements 2011, the scattering elements may be provided as to correspond to the respective support members of the microlens array. For example, scattering member 2011 may be provided at a location of optical waveguide 201 below a corresponding support member of a microlens array.

In one embodiment, imaging component 203 may include a plurality of imaging units. Imaging component 203 may include a first imaging unit 213, a second imaging unit 223, a third imaging unit 233, as shown in FIG. 2A. Each imaging unit may include a plurality of pixels. Each imaging unit corresponds to a microlens to receive at least a portion of the light passing through the microlens for forming an image.

In one embodiment, optical waveguide 201, microlens array 202, and imaging component 203 shown in FIG. 2A may be configured such that a spot formed by light transmitting from the desired imaging portion of the surface of the to be tested substrate and passing through optical waveguide 201 and microlens array 202 and incident on the imaging plane of imaging component 203 satisfies the diffraction limit requirement, i.e., the spot is less than the size of the Airy disk. In one embodiment, the sum of the thickness of optical waveguide 201, the thickness of microlens array 202, and the spacing (air gap) between optical waveguide 201 and microlens array 202 is less than or equal to 20 µm. In a specific embodiment, the thickness of optical waveguide 201, the thickness of microlens array 202, and the air gap between optical waveguide 201 and microlens array 202 each are less than or equal to 10 µm.

As will be described in more detail below, the substrate surface defect detection device provided by the present disclosure can detect a surface defect of the substrate by the imaging of the microlens array. Since the microlens array includes a plurality of microlenses, the image of the substrate surface at different locations of the substrate can be obtained by moving the substrate only one time, so that the detection speed of the surface defects of the substrate can be increased.

Figure 2B:
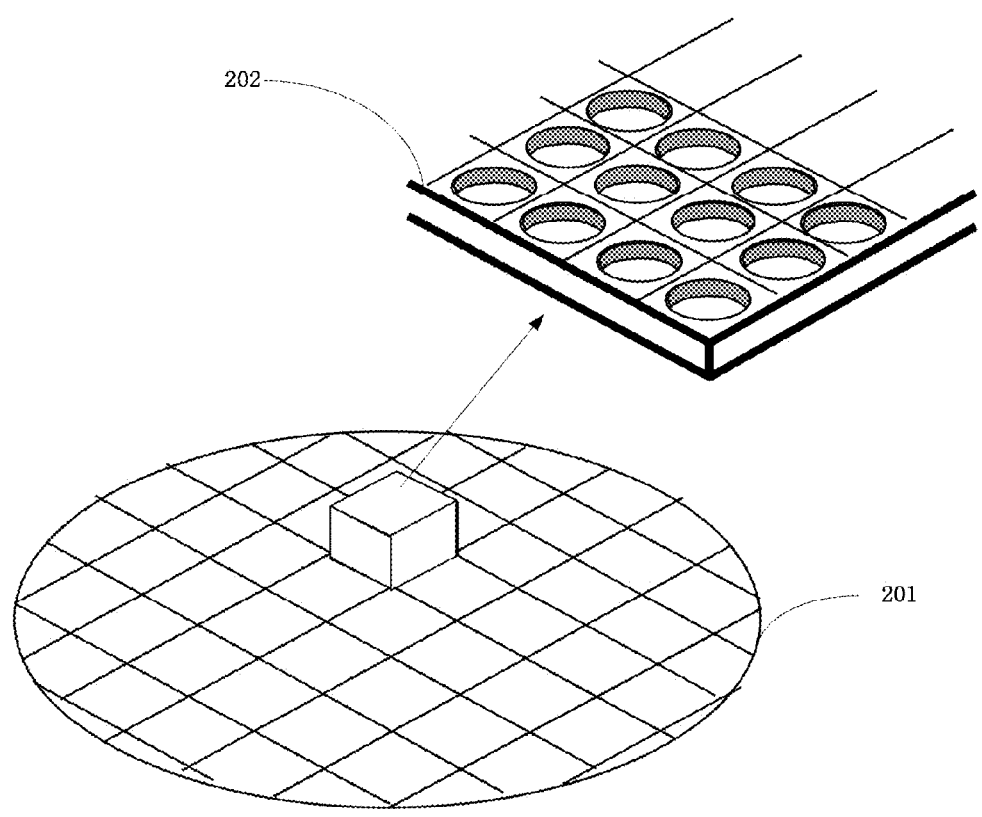
FIG. 2B is a perspective view illustrating the positional relationship between the microlens array and the substrate surface according to an embodiment of the present disclosure.

In practical applications, the substrate surface defect detection speed can be improved multiple times by setting the size of the microlens array, the diameter of the microlens, and the field of view of the microlens. For example, in the case where the diameter of the microlens is 10 µm, the size of the microlens can be set to be the same as the exposure area, as shown in FIG. 2B. In the case where any imaging point of the microlens in the field of view of 1 µm×1 µm satisfies the diffraction limit, an exposure area can be completely scanned using 100 pictures, the detection speed can be increased to 10,000 (ten thousands) times over the current techniques. In the case where any imaging point of the microlens in the field of view of 2 µm×2 µm satisfies the diffraction limit, an exposure area can be completely scanned using 25 pictures, the detection speed can be improved to 40,000 times over the current techniques.

Of course, it will be appreciated that the size of the microlens array may also be set to be different from the exposure area, and it is still possible to increase the defect detection speed. For example, the microlens array may be set to an array of 100×100 microlenses, or 1000×1000 microlenses.

It is to be noted that the microlenses in the microlens array may include, but are not limited to, a plano-convex lens element, a convex lens element, convex-concave (meniscus) lens element, etc., as long as the microlens can converge light.

In practical applications, a plano-convex lens element is preferred to the convenience of processing and assembling of the microlenses. Because the plano-convex lens element includes a plane, the use of the plano-convex microlenses makes the processing and assembling easier, thereby reducing the manufacturing cost of the microlens array.

Figure 3:
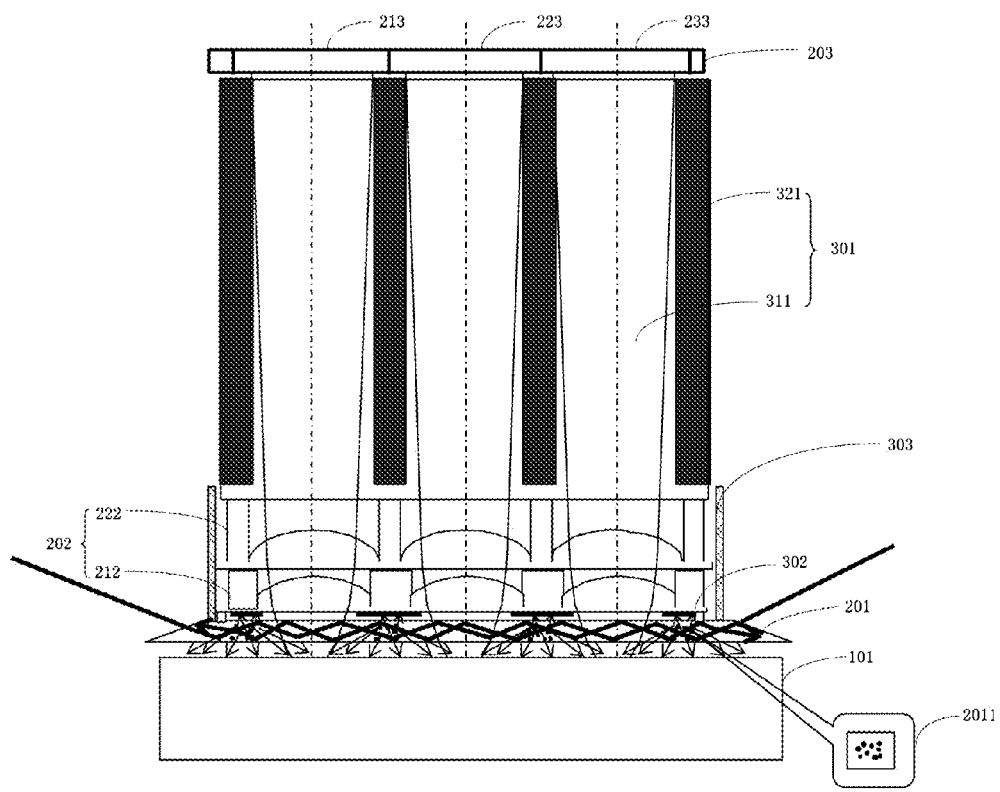
FIG. 3 is a schematic cross-sectional view of a substrate surface defect detection apparatus according to an embodiment of the present disclosure.

FIG. 3 is a schematic view of a substrate surface defect detection device according to another embodiment of the present disclosure. As shown in FIG. 3, the substrate surface defect detection device may further include a plurality of light confinement members 301 disposed between the corresponding imaging unit of the imaging component and the microlens of the microlens array. Light confinement members 301 are configured to enable the light from the corresponding microlens to reflect a specific field of view to pass through and into the corresponding imaging unit. In one embodiment, light confinement members 301 each may include a cylindrical optical member 311 and a light blocking plate 321. Cylindrical optical members 311 each include a light receiving surface and a light exit surface, and light from a corresponding microlens reflecting a specific field of view enters cylindrical optical member 311 through the light receiving surface and enters a corresponding image forming unit through the light exit surface. In one embodiment, the distance between the surface of the to be tested substrate 101 and the light receiving surface of the light receiving surface of cylindrical optical member 311 is less than or equal to 20 µm. Light blocking plate 321 may surround the peripheral surface of cylindrical optical member 311 with the exception of the light receiving surface and the light exit surface so that light from the corresponding microlens reflecting the specific field of view does not enter adjacent imaging units. It is to be understood that the above-described specific field of view may be a field of view of different dimensions dependent on the optical waveguide and the parameters of the microlens, e.g., a field of view of 1 µm×1 µm, 2 µm×2 µm, etc. However, in other embodiments, light confinement members 301 each may include only light blocking member 321. As a non-limiting exemplary embodiment, light blocking member 321 may be metal, polysilicon, or carbon powder.

In one embodiment, optical waveguide 201, microlens array 202, cylindrical optical element 311, and imaging component 203 shown in FIG. 3 may be configured such that a spot formed by light from the desired imaging portion of the to be tested substrate 101 passes through optical waveguide 201, microlens array 202, and cylindrical optical element 311 and incident to imaging component 203 satisfies the diffraction limit requirement, i.e., the spot is less than the size of the Airy disk.

In the microlens array having the support member, the support member may be formed of the same material as the microlens, for example, quartz glass. In this case, light transmitted in optical waveguide 201 may enter the support member, thereby entering the microlens and affecting the imaging quality of the microlens. In order to eliminate this effect, in one embodiment, the substrate surface defect detection device may further include a barrier layer 302 disposed on the lower surface of the support member and/or on a portion of the second surface of optical waveguide 201 under the support member, as shown in FIG. 3. Barrier layer 302 is configured to block light entering into the support member. Barrier layer 302 may include a metal plating layer.

Further, undesired light such as ambient light may also enter the microlens through the side of the microlens array, thereby affecting the imaging quality of the microlens. In order to eliminate this effect, in one embodiment, the substrate surface defect detection device may further include a spacer 303 disposed at the sides of microlens array 202 for blocking ambient light from entering the microlenses, thereby preventing ambient light from affecting the imaging quality of the microlenses, as shown in FIG. 3.

For a substrate surface defect detection device having a microlens array, the distance between the microlenses and the substrate surface is small, e.g., only a few microns (µm), which presents a requirement for high radiance of illumination. The present disclosure provides the following solution to the illumination problem of the substrate surface defect detection device.

Figure 4:
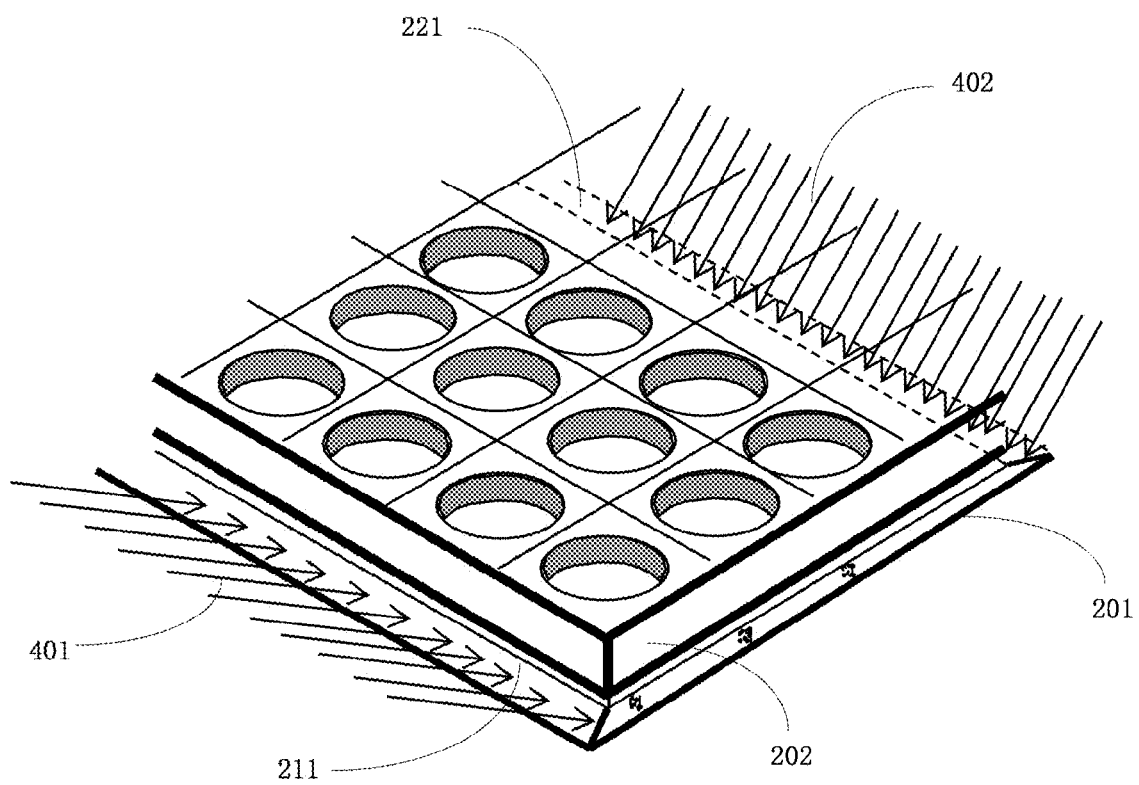
FIG. 4 is a perspective view illustrating a side illumination of the microlens array from an optical waveguide according to an embodiment of the present disclosure.

FIG. 4 is a perspective view illustrating a side illumination of the microlens array from an optical waveguide according to an embodiment of the present disclosure. Referring to FIG. 4, optical waveguide 201 may include a first incident surface 211 and a second incident surface 221 on opposite sides of the optical waveguide. Incident light on optical waveguide 201 may include a first incident light 401 and a second incident light 402 entering optical waveguide 201 from respective first incident surface 211 and second incident surface 221 of the optical waveguide. In one embodiment, the light intensity of first incident light 401 and second incident light 402 can be substantially the same, so that the uniformity of incident light on the surface of the to be tested substrate is improved, and the uniformity of the incident light received from the substrate surface to be measured by the microlenses is also improved, so that the image distortion caused by the inhomogeneity of incident can be reduced. For example, first incident light 401 and second incident light 402 may be ultraviolet light. In one embodiment, first incident light 401 and second incident light 402 may be ultraviolet light having a wave length of about 193 nm (e.g., 192.5 to 193.5 nm). Of course, the present disclosure is not limited thereto.

In one embodiment, first incident surface 211 and second incident surface 221 are inclined with respect to the first surface of optical waveguide 201 so that the incident angles of first incident light 401 and second incident light 402 can be more easily adjusted so that first incident light 401 and second incident light 402 are transmitted in the optical waveguide in a totally reflective manner. For example, the angles between first incident surface 211 and second incident surface 221 and the first surface (i.e., the bottom surface of optical waveguide 201) each can be an acute angle.

Figure 5:
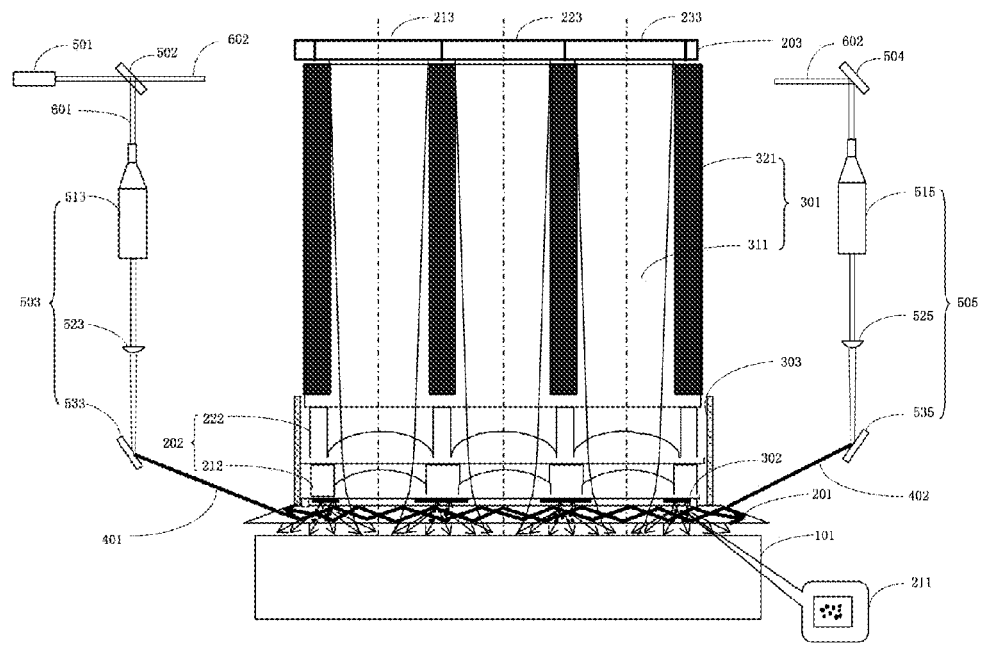
FIG. 5 is a schematic cross-sectional view of a substrate surface defect detection apparatus according to an embodiment of the present disclosure.

FIG. 5 is a schematic view of a substrate surface defect detection apparatus according to an embodiment of the present disclosure. Referring to FIG. 5, the substrate surface defect detection device may further include a laser light source 501, a semitransparent mirror 502, and a first light generating member 503 for generating first light. Laser light source 501 is configured to generate a laser beam, e.g., ultraviolet light having a wavelength of about 193 nm. Semitransparent mirror 502 is disposed at an angle relative to the optical axis of the laser light source and configured to split the laser beam into first partial light (reflected light) 601 and second partial light (transmitted light) 602. First light generating member 503 includes a first beam expander 513, a first lens 523, and a first mirror 533. First beam expander 513 is configured to expand the first portion of the light from semitransparent mirror 502 in the first dimension (in the dimension perpendicular to the drawing plane as shown in FIG. 5) to generate a first laser beam after the beam expansion. First lens 523 is configured to converge the beam of the first laser beam after the beam expansion in a second dimension different from the first dimension (in the dimension parallel to the drawing plane in the horizontal direction) to generate the converged first laser beam after the beam convergence. First mirror 533 is configured to reflect the converged first laser beam so as to be incident on the first incident surface of optical waveguide 201 as first light 401.

Referring still to FIG. 5, the substrate surface defect detection device may further include a second mirror 504 and a second light generating member 505 for generating second light. Second mirror 504 is configured to reflect second partial light 602 from laser light source 501. Second light generating member 505 may include a second beam expander 515, a second lens 525, and a third mirror 535. Second beam expander 515 is configured to expand the first portion of the light from semitransparent mirror 502 in the first dimension (e.g., in the dimension perpendicular to the drawing plane as shown in FIG. 5) to generate a second laser beam after the beam expansion. Second lens 525 is configured to converge the expanded second laser beam after the beam expansion in the second dimension different from the first dimension (e.g., in the dimension parallel to the drawing plane in the horizontal direction) to generate the converged second laser beam after the beam convergence. Third mirror 535 is configured to reflect the converged second laser beam so as to be incident on the second incident surface of optical waveguide 201 as second light 402.

Figure 6:
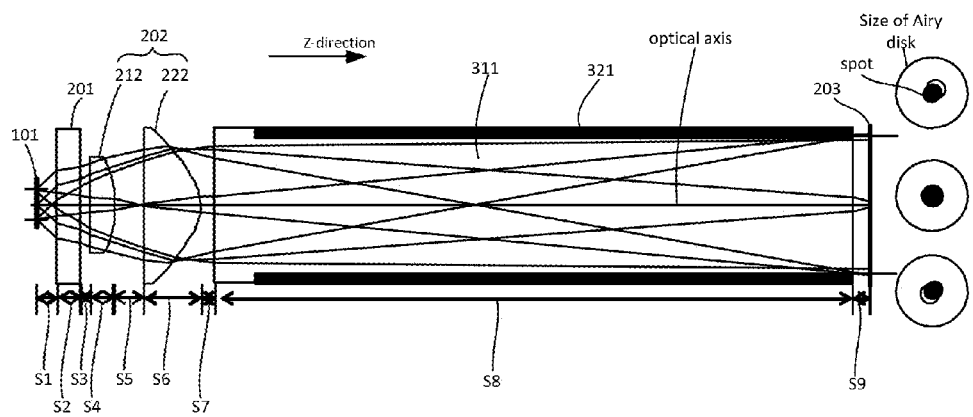
FIG. 6 is a schematic cross-sectional view of a structure of a substrate surface defect detection apparatus according to an embodiment of the present disclosure.

FIG. 6 is a schematic view of a structure of a substrate surface defect detection apparatus according to an embodiment of the present disclosure. Referring to FIG. 6, the distance S1 between substrate 101 and the first surface of optical waveguide 201 may be in the range between 1 μm and 3 μm; the thickness S2 of optical waveguide 201 may be about 2 μm; the distance S3 between the second surface of optical waveguide 201 and first microlens array 212 may be in the range between 0.5 μm and 1 μm; the thickness S4 of first microlens array 212 may be in the range between 1 μm and 6 μm; the distance S5 between first microlens array 212 and second microlens array 222 may be in the range between 1 μm and 5 μm; the thickness S6 of second microlens array 222 may be in the range between 1 μm and 3 μm; the distance S7 between second microlens array 222 and cylindrical optical member 311 may be in the range between 0.5 μm and 1.5 μm; cylindrical optical member 311 has a length S8 in the range between 30 μm and 120 μm; the distance S9 between second cylindrical optical member 311 and imaging component 203 may be in the range between 0.5 μm and 1.5 μm.

The parameters of the components of the substrate surface defect detection device are described below in two specific embodiments.

In the following embodiments, the microlens may be a plano-convex lens. In one embodiment, the coordinates of the Z-direction (parallel to the optical axis) of a point on the aspheric surface of the convex lens may be a second order function term to a fourth order function term of the distance r of a corresponding plane projection point on the plane perpendicular to the optical axis. Further, the aspheric surface of the convex lens can be expressed using the following expression:

$$Z = \frac{\frac{1}{R}r^2}{1+\sqrt{1-(1+K)\frac{r^2}{R^2}}} + \alpha_1 r^2 + \alpha_2 r^4$$

where r is the distance from the point of the aspheric surface perpendicular to the optical axis, Z is the coordinate of the point on the aspheric surface of the lens in the Z-direction (i.e., the height of a point on the aspheric surface at a distance r from the optical axis relative to the tangential plane at the aspheric surface vertex), R is the radius of curvature from the optical axis to the lens surface, K is a conic constant, α1 is an aspheric surface coefficient of the second order term, and α2 is an aspheric surface coefficient of the fourth order term. For a plano-convex lens, K is 0 (zero).

In one embodiment, the aspheric surface of the microlens of first microlens array 212 can be expressed using the following expression:

$$Z = \frac{\frac{1}{5.503}r^2}{1+\sqrt{1-\frac{r^2}{5.503^2}}} - 128.604r^2 - 1.59 \times 10^6 r^4$$

the aspheric surface of the microlens of second microlens array 222 can be expressed using the following expression:

$$Z = \frac{\frac{1}{-1.206}r^2}{1+\sqrt{1-\frac{r^2}{(-1.206)^2}}} - 97.857r^2 - 7.285 \times 10^4 r^4$$

In the embodiment, the diameter of first microlens array 212 and second microlens array 222 may be set to 10 μm. The microlens array formed by first microlens array 212 and second microlens array 222 has a numerical aperture of 0.7 and a 9× magnification. In this case, the value of the parameters S1 through S9 may be set as follows: S1 is about 1.5 μm, S2 is about 2 μm, S3 is about 0.5 μm, S4 is about 2 μm, S5 is about 1.3 μm, S6 is about 3 μm, S7 is about 1 μm, S8 is about 95 μm, and S9 is about 1 μm. In the case where the filed of view is 1 μm×1 μm, a spot formed by light from the desired imaged portion of the surface of the to be tested substrate 101 passing through optical waveguide 201, microlens array 202 and cylindrical optical member 311 is incident on imaging member 203 satisfies the diffraction limit requirement, i.e., the size (inner circle) of the actual spot is smaller than the size of the Airy disk (outer circle). At this point, the depth of focus can be extended to ±0.31 the maximum distortion is about 0.30%, about 3 nm. The embodiment enables the defect detection speed to be 10,000 times faster than the defect detection speed of a conventional substrate surface defect detection device.

In another embodiment, the aspheric surface of the microlens of first microlens array 212 can be expressed using the following expression:

$$Z = \frac{\frac{1}{9.995}r^2}{1+\sqrt{1-\frac{r^2}{9.995^2}}} - 29.93r^2$$

the aspheric surface of the microlens of second microlens array 222 can be expressed using the following expression:

$$Z = \frac{\frac{1}{28}r^2}{1+\sqrt{1-\frac{r^2}{28^2}}} - 43.969r^2$$

In the embodiment, the diameter of first microlens array 212 and second microlens array 222 may be set to 10 μm. The microlens array formed by first microlens array 212 and second microlens array 222 has a numerical aperture of 0.9 and a 5× magnification. In this case, the value of the parameters S1 through S9 may be set as follows: S1 is about 1.5 μm, S2 is about 2 μm, S3 is about 0.5 μm, S4 is about 5 μm, S5 is about 4.5 μm, S6 is about 3 μm, S7 is about 1 μm, S8 is about 40 μm, and S9 is about 1 μm. In the case where the filed of view is 2 μm×2 μm, a spot formed by light from the desired imaged portion of the surface of the to be tested substrate 101 passing through optical waveguide 201, microlens array 202 and cylindrical optical member 311 is incident on imaging member 203 satisfies the diffraction limit requirement, i.e., the size (inner circle) of the actual spot is smaller than the size of the Airy disk (outer circle). At this point, the depth of focus can be extended to ±5 μm. The embodiment enables the defect detection speed to be 40,000 times faster than the defect detection speed of a conventional substrate surface defect detection device.

It is to be understood that both embodiments described above are merely exemplary and are not intended to limit the scope of the present disclosure. Those of skill in the art can adjust the parameters of the components in the substrate surface defect detection device in accordance with the teachings of the present disclosure so the spots formed on the imaging plane of the imaging member in different field of view satisfy the diffraction limit requirement so that the defect detection speed can be improved by several orders of magnitude.

For a single microlens, the distortion of the image may be very small. However, image distortion may be severe when the cumulative effect of the microlenses is taken into consideration. Therefore, after imaging with the above-described image forming member, the resulting image may be deviated from the desired location due to the presence of distortion. In view of this problem, the present disclosure also provides a method and apparatus for correcting image distortion that will be described in detail below.

Figure 7:
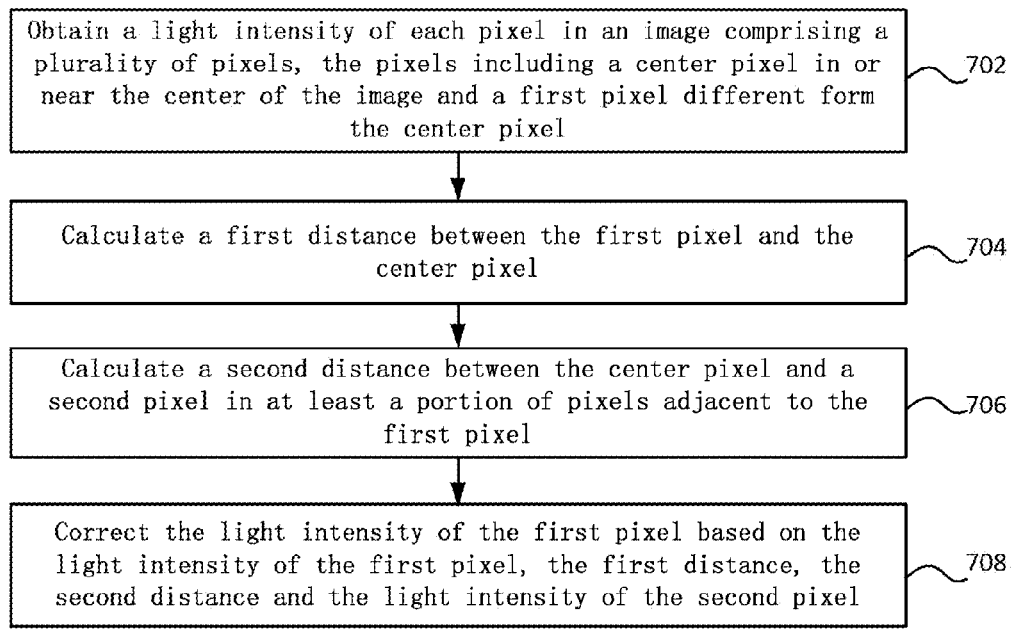
FIG. 7 is a simplified flowchart of a method for image distortion correction according to an embodiment of the present disclosure.

FIG. 7 is a simplified flowchart of a method for image distortion correction according to an embodiment of the present disclosure. The method may include the following steps:

Step 702: obtaining a light intensity of each pixel in an image comprising a plurality of pixels, the plurality of pixels may include a center pixel located in the center or near the center of the image and a first pixel different from the center pixel.

The image comprising the plurality of pixels maybe an image formed by imaging unit 203 that receives light from the microlens array. The center pixel may be in the center of the image, or in the vicinity of the center of the image, or defined by the user at a location of the image.

Step 704: calculating (computing using a computer) a first distance between the first pixel and the center pixel.

Step 706: calculating a second distance between the center pixel and a second pixel in at least a portion of the pixels adjacent to (in the vicinity of) the center pixel.

The portion of the pixels adjacent to the center pixel may include a plurality of pixels, and the second pixel may include a portion of the portion of the pixels adjacent to the center pixel, or the second pixel may include the entire portion of the pixels adjacent to the center pixel. In one embodiment, the second pixel is not the center pixel.

Step 708: correcting the light intensity of the first pixel based on the light intensity of first pixel, the first distance, the second distance, and the light intensity of the second pixel.

The method for correcting an image distortion according to the present disclosure can correct the light intensity of the first pixel based on the light intensity of the first pixel and the light intensity of at least a portion of the second pixel adjacent to the first pixel, so that the obtained image can be made closed to the actual image.

Figure 8A:
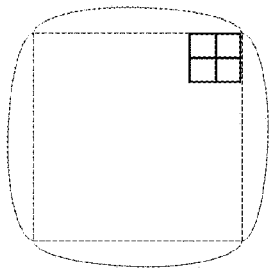
FIG. 8A is a schematic view of a barrel-shaped distortion according to an embodiment of the present disclosure.
Figure 8B:
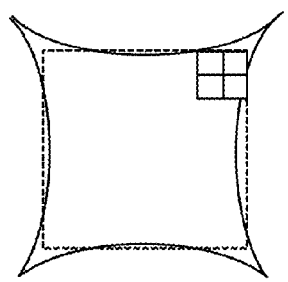
FIG. 8B is a schematic view of a pillow-shaped distortion according to an embodiment of the present disclosure.

In general, the distortion in the microlens imaging process may include two main types: one type is barrel distortion, as shown in FIG. 8A. The other type is pin-cushion distortion, as shown in FIG. 8B. In FIGS. 8A and 8B, the dotted lines represent the ideal image of the imaging unit without distortion. The four small boxes represent four adjacent pixels. For these two distortion types, the distortion correction can be implemented in different ways and will be described in detail below.

Figure 9A:
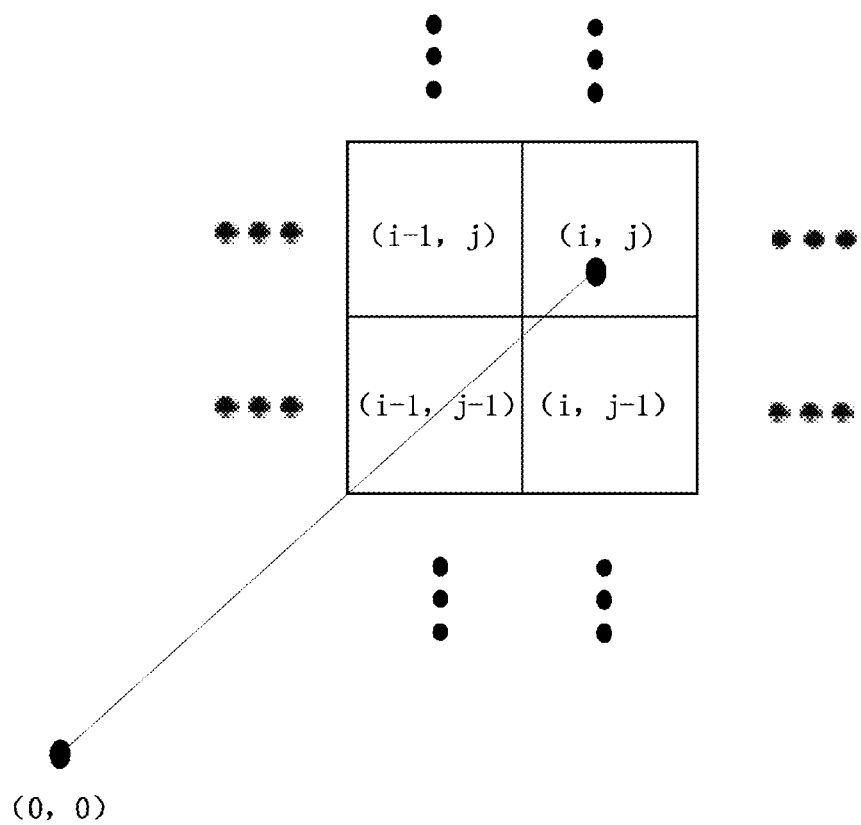
FIG. 9A shows a correction of a first pixel according to an embodiment of the present disclosure.

In one embodiment, the light intensity of the first pixel may be corrected based on the light intensity of the first pixel and the light intensity of the three pixels whose second distance is smaller than the first distance of the first pixel to the center pixel. Referring to FIG. 9A, the coordinates of the first pixel are (i, j), the coordinates of the center pixel are (0, 0), the pixel (i−1, j−1), the pixel (i−1, j), and the pixel (i, j−1) are pixels that are closer to the center pixel (0, 0) than the first pixel (i, j). That is, the second distance of the three pixels from the center pixel is smaller than the first distance of the first pixel (i, j) from the center pixel (0, 0). Specifically, the light intensity of the first pixel can be corrected using the following expression:

$$\overline{P_{(i,j)}} = C_1 P_{(i,j)} + C_2 P_{(i-1,j-1)} + C_3 P_{(i-1,j)} + C_4 P_{(i,j-1)}$$

where i, j are non-zero integers, C1, C2, C3, C4 are the correction coefficients and C1+C2+C3+C4=1, $P_{(i, j)}$ is the light intensity of the first pixel (i, j), and $\overline{P_{(i,j)}}$ is the corrected light intensity of the pixel (i, j).

This correction method is suitable for the image having the barrel distortion as shown in FIG. 8A. The light intensity of the first pixel can be corrected using the original light intensity of the first pixel and the light intensity of the three adjacent pixels closer to the center pixel than the first pixel so that the image having the barrel distortion can be corrected.

Figure 9B:
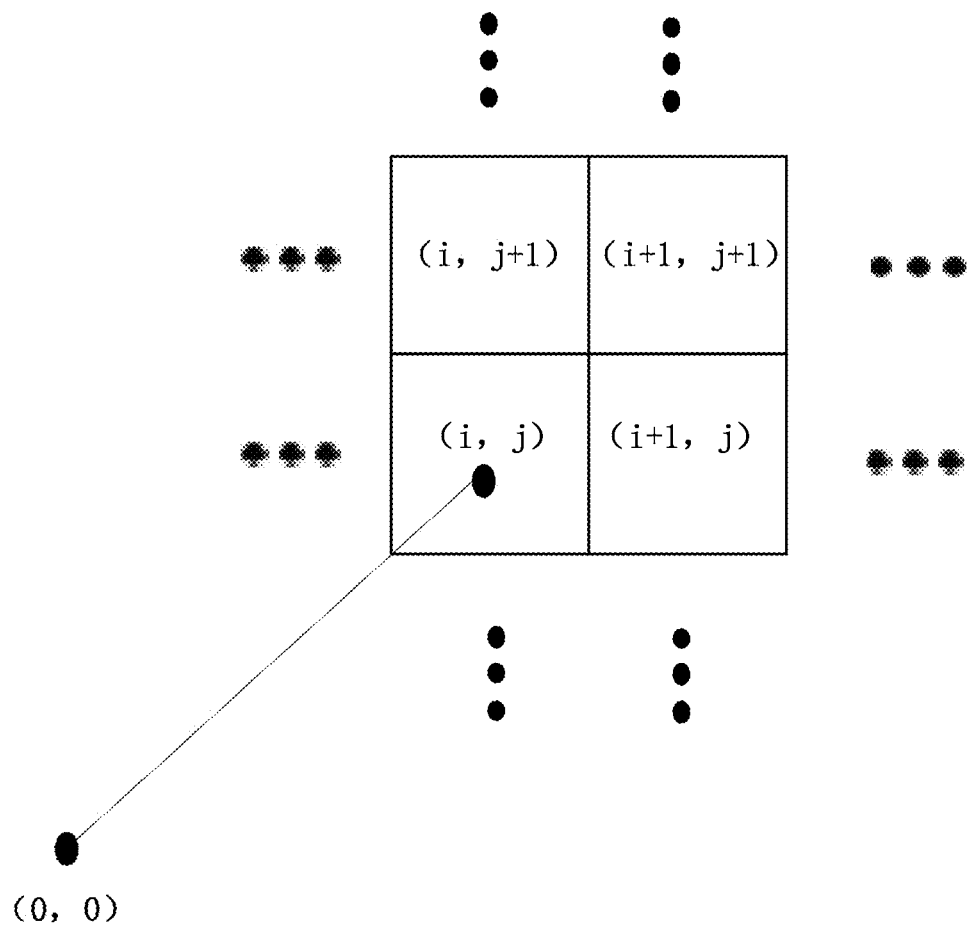
FIG. 9B shows a correction of a first pixel according to an embodiment of the present disclosure

In another embodiment, the light intensity of the first pixel may be corrected based on the light intensity of the first pixel and the light intensity of the three pixels whose second distance is greater than the first distance of the first pixel to the center pixel. Referring to FIG. 9B, the coordinates of the first pixel are (i, j), the coordinates of the center pixel are (0, 0), the pixel (i+1, j+1), the pixel (i+1, j), and the pixel (i, j+1) are pixels that are farther away from the center pixel (0, 0) than the first pixel (i, j). That is, the second distance of the three pixels from the center pixel is greater than the first distance of the first pixel (i, j) from the center pixel (0, 0). Specifically, the light intensity of the first pixel can be corrected using the following expression:

$$\overline{P_{(i,j)}} = C_1 P_{(i,j)} + C_2 P_{(i+1,j+1)} + C_3 P_{(i+1,j)} + C_4 P_{(i,j+1)}$$

where i, j are non-zero integers, C1, C2, C3, C4 are the correction coefficients and C1+C2+C3+C4=1, $P_{(i, j)}$ is the light intensity of the first pixel (i, j), and $\overline{P_{(i,j)}}$ is the corrected light intensity of the pixel (i, j).

This correction method is suitable for the image having the pin-cushion distortion as shown in FIG. 8B. The light intensity of the first pixel can be corrected using the original light intensity of the first pixel and the light intensity of the three adjacent pixels that are farther away from the center pixel than the first pixel so that the image having the pin-cushion distortion can be corrected.

The present disclosure thus provides methods for correcting an image having distortion. It can be assuming that the size and trend of the distortion amount of each microlens are the same so that the processing efficiency of the image pattern can be improved.

The present disclosure also provides a correction device for correcting image distortion.

Figure 10:
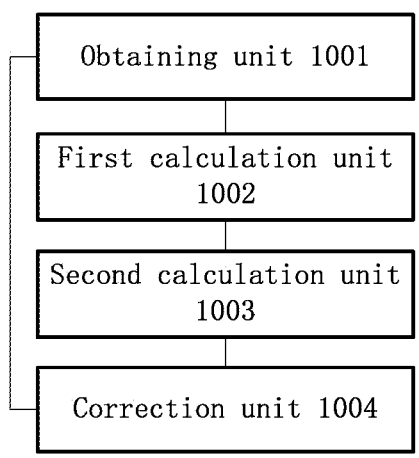
FIG. 10 is a simplified block diagram of a image distortion correction apparatus according to an embodiment of the present disclosure.

FIG. 10 is a simplified block diagram of an image distortion correction device according to an embodiment of the present disclosure. Referring to FIG. 10, the image distortion correction device include an obtaining unit 1001, a first calculation unit 1002, a second calculation unit 1003, and a correction unit 1004. Obtaining unit 1001 is configured to obtain the light intensity of each pixel in an image including a plurality of pixels. The plurality of pixels may include a center pixel disposed at the center or near the center of the image and a first pixel different form the center pixel. First calculation unit 1002 is configured to calculate the first distance between the first pixel and the center pixel. Second calculation unit 1003 is configured to calculate a second distance between a second pixel and the first pixel, the second pixel may be at least a portion of the pixels adjacent to the first pixel. Correction unit 1004 is configured to correct the light intensity of the first pixel based on the original light intensity of the first pixel, the first distance, the second distance and the light intensity of the second pixel.

The image distortion correction device according to the present invention can correct the light intensity of the first pixel using the originally obtained light intensity of the first pixel and of the second pixel that includes at least a portion of the pixels adjacent to the first pixel, so that the resulting image can be made closer to the actual image. In practical applications, the function of the image distortion correction device can be implemented by hardware (e.g., circuit logic, FPGA, one or more processing units) or by software having program code and instructions stored in a computer readable storage medium.

For different distortion types, correction unit 1004 may correct the light intensity of the first pixel using different approaches.

In one embodiment, the image may have a barrel distortion. Referring to FIG. 9A, the coordinates of the first pixel are (i, j), the coordinates of the center pixel are (0, 0), the pixel (i−1, j−1), the pixel (i−1, j), and the pixel (i, j−1) are pixels that are closer to the center pixel (0, 0) than the first pixel (i, j). That is, the second distance of the three pixels from the center pixel is smaller than the first distance of the first pixel (i, j) from the center pixel (0, 0). Specifically, the light intensity of the first pixel can be corrected using the following expression:

$$\overline{P_{(i,j)}} = C_1 P_{(i,j)} + C_2 P_{(i-1,j-1)} + C_3 P_{(i-1,j)} + C_4 P_{(i,j-1)}$$

where i, j are non-zero integers, C1, C2, C3, C4 are the correction coefficients and C1+C2+C3+C4=1, $P_{(i,\,j)}$ is the light intensity of the first pixel (i, j), and $\overline{P_{(i,j)}}$ is the corrected light intensity of the pixel (i, j).

In another embodiment, the image may have a pincushion distortion. Referring to FIG. 9B, the coordinates of the first pixel are (i, j), the coordinates of the center pixel are (0, 0), the pixel (i+1, j+1), the pixel (i+1, j), and the pixel (i, j+1) are pixels that are farther away from the center pixel (0, 0) than the first pixel (i, j). That is, the second distance of the three pixels from the center pixel is greater than the first distance of the first pixel (i, j) from the center pixel (0, 0). Specifically, the light intensity of the first pixel can be corrected using the following expression:

$$\overline{P_{(i,j)}} = C_1 P_{(i,j)} + C_2 P_{(i+1,j+1)} + C_3 P_{(i+1,j)} + C_4 P_{(i,j+1)}$$

where i, j are non-zero integers, C1, C2, C3, C4 are the correction coefficients and C1+C2+C3+C4=1, $P_{(i,\,j)}$ is the light intensity of the first pixel (i, j), and $\overline{P_{(i,j)}}$ is the corrected light intensity of the pixel (i, j).

The present disclosure also provides a substrate surface defect detection device that may be any one of the above-described substrate surface defect detection devices and a device for correcting image distortion that may be one of the above-described image distortion correction devices.

Figure 11:
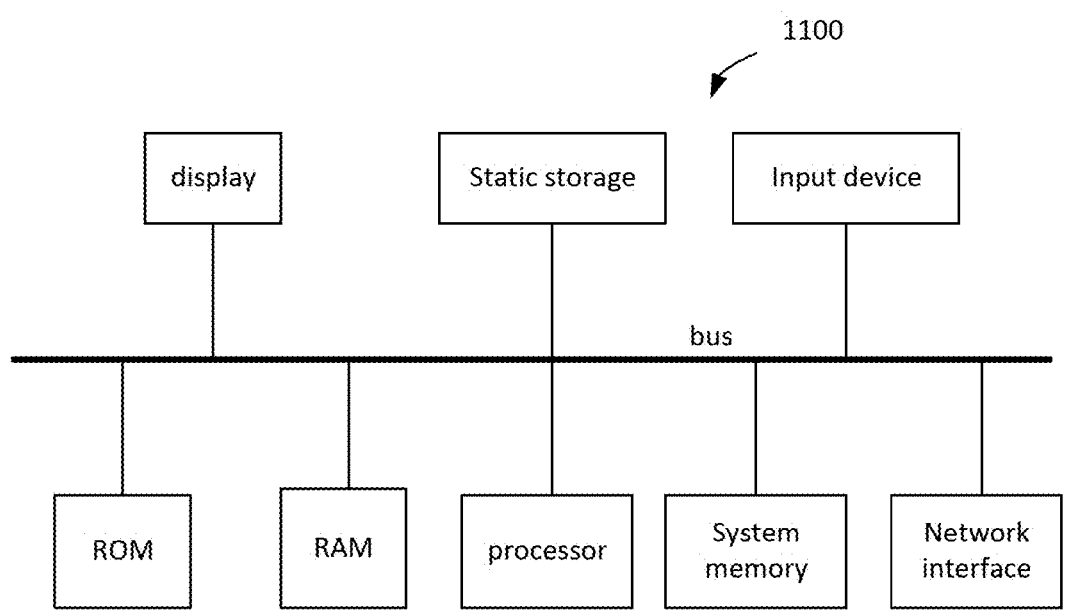
FIG. 11 is a simplified block diagram of a computing apparatus that may be programmed to execute codes for correcting image distortion according to one embodiment of the present disclosure.

FIG. 11 is a simplified block diagram of a computing apparatus 1100 that may be programmed to execute codes for correcting image distortion according to one embodiment of the present disclosure. As shown, computing apparatus 1100 includes a processor having one or more processing units, a system memory, static storage units (hard drive), a display unit (LCD), an input device (keyboard, mouse, optical disc or magnetic tape reader, and the like). Computer apparatus 1100 also includes a network interface unit configured to connect the computing apparatus with other devices through a local area network, a wide area network, or a wireless network. In an embodiment, the display unit has one or more windows for displaying the obtained light intensity of each pixel of an image, the image distortion and the corrected image. The input device may be connected to a digital camera for obtaining the light intensity of each pixel of an image. The processor is configured to calculate or compute the first distance between the first pixel and the center pixel, the second distance between the center pixel and the second pixel, and correct the light intensity of the first pixel based on the obtained light intensity of the first and second pixel, the first distance, and the second distance. The computing apparatus shown in FIG. 11 may include instruction codes that are stored in the system memory and executable by the processor to perform the above-described distance calculation and distortion correction.

The terms "device" and "apparatus" are used interchangeably. The terms "computing" and "calculating" are used interchangeably.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While the present disclosure is described herein with reference to illustrative embodiments, this description is not intended to be construed in a limiting sense. Rather, the purpose of the illustrative embodiments is to make the spirit of the present disclosure be better understood by those skilled in the art. In order not to obscure the scope of the disclosure, many details of well-known processes and manufacturing techniques are omitted. Various modifications of the illustrative embodiments as well as other embodiments will be apparent to those of skill in the art upon reference to the description. It is therefore intended that the appended claims encompass any such modifications.

Furthermore, some of the features of the preferred embodiments of the present disclosure could be used to advantage without the corresponding use of other features. As such, the foregoing description should be considered as merely illustrative of the principles of the disclosure, and not in limitation thereof.

What is claimed is:

1. A substrate surface defect detection device, comprising:
   an optical waveguide for receiving first light and directing the received first light to a surface of a to be tested substrate, the optical waveguide having a first surface facing toward the substrate and a second surface facing away from the substrate;

at least one microlens array disposed on the second surface of the optical waveguide, the at least one microlens array comprising a plurality of microlenses arranged in an array for receiving second light from the surface of the to be tested substrate and converging the received second light to converged light; and an imaging component for receiving the converged light from the at least one microlens array for optical imaging, wherein the imaging component comprises a plurality of imaging units, each of the imaging units comprising a plurality of pixels, each of the imaging units being associated with one of the microlenses to receive a portion of the converged light.

2. The substrate surface defect detection device of claim 1, wherein the at least one microlens array comprises:

a first microlens array and a second microlens array stacked over each other, the first and second microlens arrays each having a plurality of microlenses, each of the microlenses of the first microlens array having an optical axis aligned to an optical axis of one corresponding microlens of the second microlens array.

3. The substrate surface defect detection device of claim 2, further comprising:

a plurality of light confinement members disposed between a corresponding imaging unit and a corresponding microlens and configured to enable light from the corresponding microlens to reflect a specific field of view to pass therethrough and into the corresponding imaging unit.

4. The substrate surface defect detection device of claim 3, wherein the light confinement members each comprise a light blocking plate.

5. The substrate surface defect detection device of claim 3, wherein the light confinement members each comprise a cylindrical optical member having a light receiving surface and a light exit surface.

6. The substrate surface defect detection device of claim 1, wherein the at least one microlens array further comprises a support member disposed at an edge of the microlenses.

7. The substrate surface defect detection device of claim 6, wherein the at least one microlens array comprises a first microlens array and a second microlens array stacked over each other, the support member of the first microlens array and the support member of the second microlens array are aligned with each other.

8. The substrate surface defect detection device of claim 6, wherein the support member is formed of a same material as a material of the microlenses and comprises a barrier layer on a lower surface for blocking light from entering the support member.

9. The substrate surface defect detection device of claim 8, wherein the barrier layer comprises a metal plating layer.

10. The substrate surface defect detection device of claim 6, wherein the support member is formed of a same material as a material of the microlenses and a surface portion of the optical waveguide below the support member comprises a barrier layer for blocking light from entering the support member.

11. The substrate surface defect detection device of claim 1, wherein the microlenses each comprises a plano-convex lens.

12. The substrate surface defect detection device of claim 11, wherein coordinates of a point on an aspheric surface of the plano-convex lens in a z-direction parallel to an optical axis has a second order function term and a fourth order function term of a distance from a corresponding plane projection point perpendicular to the optical axis.

13. The substrate surface defect detection device of claim 11, wherein a aspheric surface of the plano-convex lens is calculated by the following expression:

$$Z = \frac{\frac{1}{R}r^2}{1+\sqrt{1-(1+K)\frac{r^2}{R^2}}} + \alpha_1 r^2 + \alpha_2 r^4$$

where r is a distance from a point of the aspheric surface perpendicular to the optical axis, Z is the coordinate of the point on the aspheric surface of the lens in the Z-direction, R is the radius of curvature from the optical axis to the lens surface, K is a conic constant, $\alpha 1$ is an aspheric surface coefficient of the second order function term, and $\alpha 2$ is an aspheric surface coefficient of the fourth order function term.

14. The substrate surface defect detection device of claim 1, wherein the optical waveguide comprises a first incident surface and a second incident surface disposed on opposite sides of the optical waveguide; the first light comprises third light and fourth light, the third light entering the optical waveguide from the first incident surface and the fourth light entering the optical waveguide from the second incident surface.

15. The substrate surface defect detection device of claim 14, wherein the first incident surface and the second incident surface are inclined with respect to the first surface of the optical waveguide.

16. The substrate surface defect detection device of claim 14, further comprising:

a laser light source for generating a laser beam;

a semitransparent mirror for splitting the laser beam into first partial light and second partial light; and a first light generating member for generating a first beam and comprising:

a first beam expander for expanding the first partial light in a first dimension to generate a first laser beam;

a first lens for converging the first laser beam in a second dimension different from the first dimension to generate a converged first laser beam; and a first mirror for reflecting the converged first laser beam as the third light entering the optical waveguide from the first incident surface.

17. The substrate surface defect detection device of claim 16, further comprising:

a second mirror for reflecting the second partial light;

a second light generating member for generating a second beam and comprising:

a second beam expander for expanding the second partial light in the first dimension to generate a second laser beam;

a second lens for converging the second laser beam in the second dimension to generate a converged second laser beam; and a third mirror for reflecting the converged second laser beam as the fourth light entering the optical waveguide from the second incident surface.

18. The substrate surface defect detection device of claim 14, wherein the third light and the fourth light have a same light intensity.

19. The substrate surface defect detection device of claim 1, further comprising:
a spacer disposed on a side of the at least one microlens array and configured to block ambient light from entering the microlenses.

20. The substrate surface defect detection device of claim 1, wherein a sum of a thickness of the optical waveguide, a thickness of the at least one microlens array, and an air gap between the optical waveguide and the at least one microlens array is less than or equal to 20 μm.

21. The substrate surface defect detection device of claim 1, wherein the microlenses each have a diameter in a range between 5 μm and 20 μm.

22. The substrate surface defect detection device of claim 1, wherein the optical waveguide comprises a plurality of scattering elements configured to scatter light transmitted by the optical waveguide onto the surface of the to be tested substrate.

23. The substrate surface defect detection device of claim 22, wherein the at least one microlens array further comprises:

a plurality of support members disposed at an edge of the microlenses and configured to support corresponding microlenses disposed thereon;

each of the plurality of scattering elements is disposed at a location of a corresponding one of the plurality of support members.

24. The substrate surface defect detection device of claim 22, wherein the substrate is one of a semiconductor wafer, a semiconductor substrate, and a display panel.

25. The substrate surface defect detection device of claim 1, wherein the optical waveguide, the at least one microlens array, and the imaging component are configured such that a spot from light of a desired imaging portion of the surface of the to be tested substrate incident on an imaging plane of the imaging component through the optical waveguide and the at least one microlens array is smaller than a size of an Airy disk.

* * * * *